US010582937B2

(12) United States Patent
Gast (10) Patent No.: US 10,582,937 B2
(45) Date of Patent: Mar. 10, 2020

(54) MEDICAL GUIDE WIRE DEVICE FOR ENDOVASCULAR-INTRALUMINAL DEVICES

(71) Applicant: Thomas Gast, Chicago, IL (US)

(72) Inventor: Thomas Gast, Chicago, IL (US)

( * ) Notice: Subject to any disclaimer, the term of this patent is extended or adjusted under 35 U.S.C. 154(b) by 588 days.

(21) Appl. No.: 15/332,828

(22) Filed: Oct. 24, 2016

(65) Prior Publication Data

US 2018/0110532 A1  Apr. 26, 2018

(51) Int. Cl.
*A61B 17/22* (2006.01)
*A61B 17/12* (2006.01)
*A61M 25/09* (2006.01)
*A61B 17/00* (2006.01)

(52) U.S. Cl.
CPC .......... *A61B 17/22* (2013.01); *A61B 17/1214* (2013.01); *A61B 17/12109* (2013.01); *A61M 25/09041* (2013.01); *A61B 2017/00938* (2013.01); *A61B 2017/00942* (2013.01); *A61B 2017/22041* (2013.01); *A61B 2017/22049* (2013.01); *A61B 2017/22081* (2013.01); *A61B 2017/22094* (2013.01); *A61M 2025/09116* (2013.01); *A61M 2025/09175* (2013.01)

(58) Field of Classification Search
CPC .............. A61B 17/22; A61B 17/22031; A61B 2017/22049; A61B 2017/22081; A61B 2017/22094; A61B 2017/00942; A61B 2017/22034; A61B 2017/22035; A61M 25/09041; A61M 2025/09116
See application file for complete search history.

(56) References Cited

U.S. PATENT DOCUMENTS

| | | | |
|---|---|---|---|
| 4,326,530 | A | 4/1982 | Fleury, Jr. |
| 4,799,496 | A | 1/1989 | Hargreaves et al. |
| 5,098,412 | A | 3/1992 | Shiu |
| 5,137,517 | A | 8/1992 | Loney et al. |
| 5,336,182 | A | 8/1994 | Lundquist et al. |
| 5,728,122 | A | 3/1998 | Leschinsky et al. |
| 5,810,012 | A | 9/1998 | Lynch et al. |
| 5,820,591 | A | 10/1998 | Thompson et al. |
| 6,190,333 | B1 | 2/2001 | Valencia |
| 6,554,842 | B2 | 4/2003 | Heuser et al. |
| 6,558,349 | B1 | 5/2003 | Kirkman |

(Continued)

OTHER PUBLICATIONS

International Search Report and Written Opinion of the International Searching Authority, dated Jan. 5, 2018, in PCT Application No. PCT/US17/57523.

*Primary Examiner* — Diane D Yabut
(74) *Attorney, Agent, or Firm* — Riley Intellectual Property Law, LLC (57) ABSTRACT

A medical guide wire device includes a base wire, a first accessory wire, and a guiding device configured to be removably coupled to the base and first accessory wires. The base wire has a first proximal end, a first distal end, a longitudinal length extending therebetween, and a flexible portion near the first distal end. The first accessory wire has a second proximal end, a second distal end, a longitudinal length extending therebetween, and a flexible portion near the second distal end. The second distal end of the first accessory wire is coupled to the base wire at a distance spaced apart from the first distal end. Upon actuating the guiding device, the flexible portion of the base wire and the flexible portion of the first accessory wire form a curve at the first distal end of the base wire and the second distal end of the first accessory wire.

24 Claims, 10 Drawing Sheets

(56) References Cited

U.S. PATENT DOCUMENTS

| | | |
|---|---|---|
| 6,824,550 B1 | 11/2004 | Noriega et al. |
| 7,288,074 B2 | 10/2007 | Swain et al. |
| 7,387,632 B2 | 6/2008 | Ouchi |
| 8,002,714 B2 | 8/2011 | Bakos |
| 8,070,693 B2 | 12/2011 | Ayala et al. |
| 8,702,625 B2 | 4/2014 | Ayala et al. |
| 8,827,927 B2 | 9/2014 | Erickson et al. |
| 9,011,351 B2 | 4/2015 | Hoshinouchi |
| 2003/0014037 A1 | 1/2003 | Thompson et al. |
| 2004/0199088 A1 | 10/2004 | Bakos et al. |
| 2006/0100544 A1 | 5/2006 | Ayala et al. |
| 2009/0023986 A1 | 1/2009 | Stewart et al. |
| 2014/0257138 A1 | 9/2014 | Hui et al. |

MEDICAL GUIDE WIRE DEVICE FOR ENDOVASCULAR-INTRALUMINAL DEVICES

FIELD OF THE DISCLOSURE

The present disclosure generally relates to a medical guide wire device and a method for advancing endovascular-intraluminal devices, and, more particularly, to a medical guide wire device having a guiding device that mounts to and directs a plurality of guide wires along a vessel.

BACKGROUND

Intraluminal catheters are commonly used for a number of endovascular medical procedures involving catheters, balloon angioplasty systems, stent delivery devices, and the like. In order to properly position an endovascular device at the desired location within the vessel, a guide wire is typically first manipulated into the proper location. Once the wire is in the correct location, the catheter is slid over the guide wire and positioned as desired. Upon positioning the catheter (or other medical device), the diagnostic or therapeutic procedure is performed.

Typically, the ends of the guide wires are pre-bent prior to insertion into the vessel and an operator then rotates the wire as needed upon reaching a branch (e.g., a branch artery) to enable the guide wire to enter the appropriate branch of the vessel. Oftentimes, the angle of the bend must be adjusted, which may require the wire to be removed, adjusted, and reinserted. Such a situation oftentimes occurs when an artery branches at a first angle and sub-branches at a second angle. Inserting the guide wires in the vessel at the second angle can be a high-risk procedure that may result in trauma to the vessel. In many cases, the desired location cannot be reached at all using the guide wire.

Additionally, limited guide wire steerability can result in greater time spent in the body and significantly elevated risk of trauma to vessel and ducts. Multiple insertions of guide wires may lead to thrombosis or dissection of the vessel.

SUMMARY

It is an object of the medical guide wire device of the present disclosure to provide an improved device for guiding wires for the placement of medical equipment through vessels and ducts. In some arrangements, the device described herein can navigate branches in vessels using manual controls that are simple and easy to actuate. In some arrangements, the manual controls can be removed from the guide wires to allow medical equipment to be slid over the guiding wires so that the equipment can be inserted into the vessel.

According to some exemplary aspects of the present disclosure, a medical guide wire device includes a base wire, a first accessory wire, and a guiding device configured to be removably coupled to the base and first accessory wires. The base wire has a first proximal end, a first distal end, a longitudinal length extending therebetween, and a flexible portion near the first distal end. The first accessory wire has a second proximal end, a second distal end, a longitudinal length extending therebetween, and a flexible portion near the second distal end. The second distal end of the first accessory wire is coupled to the base wire at a distance spaced apart from the first distal end. Upon actuating the guiding device, the flexible portion of the base wire and the flexible portion of the first accessory wire form a curve at the first distal end of the base wire and the second distal end of the first accessory wire in a first direction.

According to some aspects of the present disclosure, a medical guide wire device for advancing endovascular-intraluminal devices includes a base wire and an accessory wire. The base wire has a first proximal end, a first distal end, a longitudinal length extending therebetween, and a flexible portion near the first distal end. The accessory wire has a second proximal end, a second distal end, a longitudinal length extending therebetween, and a flexible portion near the second distal end. The second distal end is coupled to the base wire at a distance spaced apart from the first distal end. In these aspects, upon moving the second proximal end of the accessory wire along a longitudinal direction relative to the base wire, the flexible portion of the accessory wire forms a bow and causes the flexible portion of the base wire to form a curve.

According to some aspects of the present disclosure, a method of using a medical guide wire device as disclosed herein includes coupling a guide wire device to a first proximal end of a base wire, coupling the guide wire device to a second proximal end of a first accessory wire, and inserting a first distal end of the base wire and a second distal end of the first accessory wire into a vessel forming an elongated cavity. The method further includes guiding the base wire and the first accessory wire through the elongated cavity with the guiding device, actuating the guiding device to cause the flexible portion of the base wire and the flexible portion of the first accessory wire to bend, and advancing the device through the elongated cavity in the direction of the bent base wire and first accessory wire.

In further accordance with any one or more of the foregoing aspects and exemplary arrangements, a medical guide wire device and/or a method of using a medical guide wire device according to the teachings of the present disclosure may include any one or more of the following optional features and/or forms.

In some arrangements, the guiding device comprises a first clamping device and a second clamping device. The first clamping device has a first clamping portion and a first guiding portion, and the second clamping device has a second clamping portion and a second guiding portion. The first clamping portion is adapted to be removably coupled to the base wire, and the second clamping portion is adapted to be removably coupled to the first accessory wire. The second guiding portion is adapted to slidably engage the first guiding portion of the first clamping device. In some forms, the first guiding portion and the second guiding portion comprise an axial track and groove assembly, such as, for example, a dovetail track adapted to be coupled with a dovetail groove. In some forms, the first guiding portion and the second guiding portion slidably engage a common base. A third guiding portion and clamping device may also be added to a common base. In some forms, the guiding portions include an axial track to be coupled with a groove assembly on a common removable base. Other examples are possible.

In some examples, the flexible portions of the base wire and the first accessory wire comprise a tapered region of reducing wire thickness. In some examples, the flexible portions of the base and first accessory wires comprise a region constructed of a different material than the remainder of the base wire and the first accessory wire. In other examples, the flexible portions can be constructed from a material that is different in shape from the remainder of the length of the wires (e.g., coiled spring and the like). Other examples and/or constructions of the flexible portions are possible. The flexible portion of the base wire may have a greater rigidity than a rigidity of the flexible portion of the accessory wire.

The base wire and/or the first accessory wire may form a circular, semi-circular, triangular, tubular, and/or rectangular cross-sectional shape. It is understood that any number of configurations or combinations are possible. The base wire and/or the first accessory wire can be coated with a hydrophilic, nonconductive (or any other) material.

In some arrangements, a tube and/or a sleeve may at least partially surround the base wire and the first accessory wire. In one possible example, to at least partially surround the base and first accessory wires, the guiding device may be removed, and the proximal ends of the base and first accessory wires may be inserted through the tube. In these examples, the tube may include a medical device which is at least partially inserted into the vessel.

In some arrangements, upon actuating the guiding device, the flexible portion of the accessory wire bows and contacts a sidewall of the vessel in a first direction. By contacting the sidewall, the first accessory wire imparts a force on the distal end of the base wire in a second direction opposite the first direction, which in turn allows the base wire to be directed through the vessel.

The medical guide wire device disclosed herein is believed to provide the user with an easy system of guiding medical wires to desired locations. Through actuation of the guiding device, the guide wire device can be selectively guided along vessels and can be directed to precise locations for placement of medical devices. By removing the guiding device, medical devices, such as, for example, catheters, occlusion balloons, and the like, can be inserted over the wires and can be placed at desired locations within the vessel while maintaining a correct position within the vessel. In some instances, the wire itself may be used as treatment by attaching devices to the tip.

Additional optional aspects, arrangements, forms, and/or advantages of the medical guide wire device disclosed herein will be apparent upon consideration of the following detailed description and the appended drawings, each different functionally operable and technically effective combination of which is expressly included as a part of the present disclosure.

BRIEF DESCRIPTION OF THE DRAWINGS

These and other aspects, arrangements, and features will be apparent from the medical guide wire device described in the following detailed description, particularly when studied in conjunction with the drawings, wherein.

DETAILED DESCRIPTION

Figure 1A:
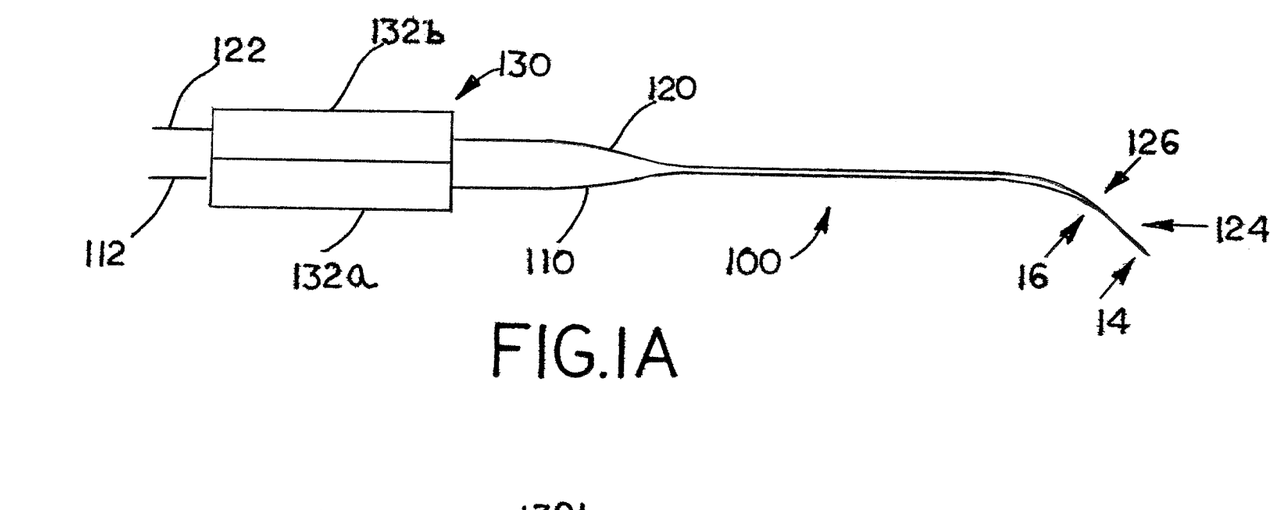
FIG. 1A is a side elevation view of a medical guide wire device assembled according to some aspects of the present disclosure with the device in a resting configuration.
Figure 1B:
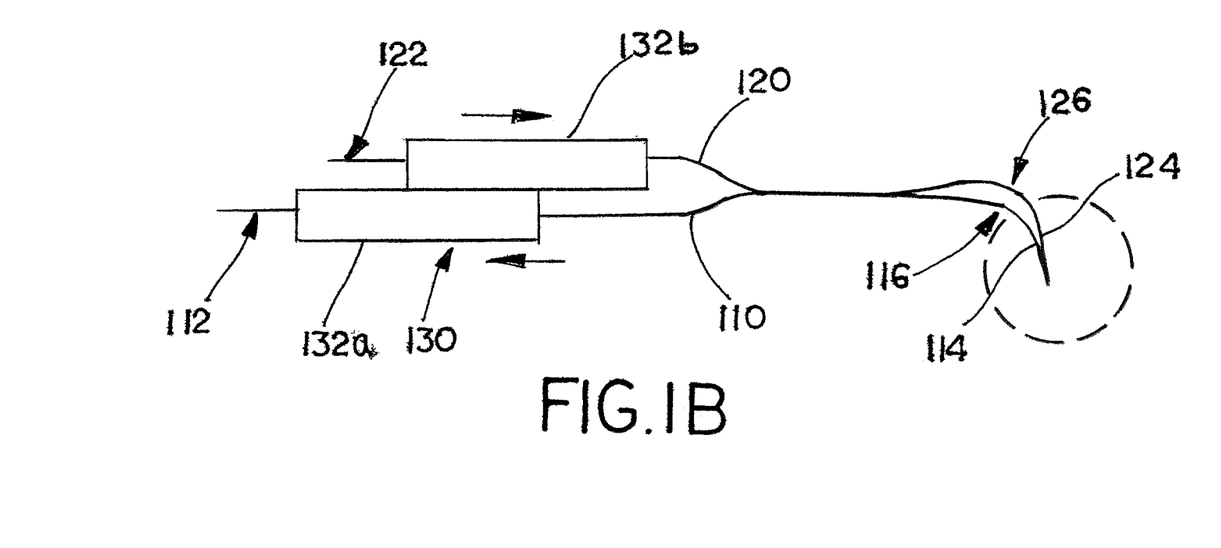
FIG. 1B is a side elevation view of the medical guide wire device in an actuated configuration.
Figure 1C:
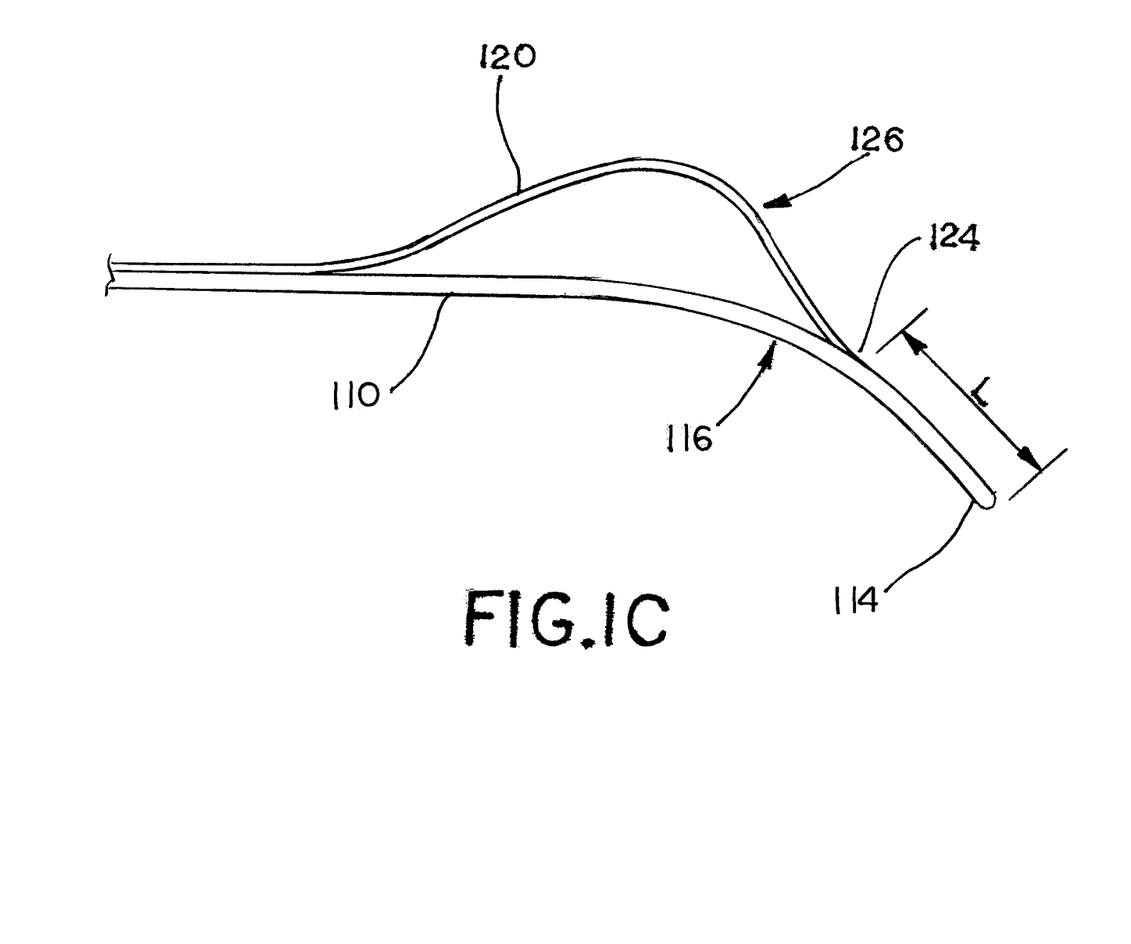
FIG. 1C is a close-up side elevation view of a first accessory wire coupled to a base wire with the device is in an actuated configuration.

Referring now to the drawings, FIGS. 1A-1C illustrate one exemplary arrangement of a medical guide wire device 100 in accordance with some aspects of the present disclosure. The medical guide wire device 100 includes a base wire 110, a first accessory wire 120, and a guiding device 130. The base wire 110 has a first proximal end 112, a first distal end 114, a longitudinal length extending between the first proximal end 112 and the first distal end 114, and a flexible portion 116 located near the first distal end 114. Similarly, the first accessory wire 120 has a second proximal end 122, a second distal end 124, a longitudinal length extending between the second proximal end 122 and the second distal end 124, and a flexible portion 126 located near the second distal end 124.

The base wire 110 and the first accessory wire 120 can be constructed from any number of generally resilient materials, such as, for example, metals and/or polymers. The base wire 110 and the first accessory wire 120 can have any number of cross-sectional shapes such as, for example, semi-circular, circular, rectangular, and tubular (as illustrated in FIGS. 8A-8F, respectively). Other examples are possible. Each of the base wire 110 and the first accessory wire 120 can be coated with a number of materials as desired. Some examples of suitable coating materials include hydrophilic materials, hydrophobic materials, conductive and nonconductive materials, and the like. Other examples are possible.

The flexible portions 116, 126 of the base and first accessory wires 110, 120 can be configured in a number of ways. In some examples, the flexible portions 116 and/or 126 can include a tapered region where a diameter of each of the base and the first accessory wires 110, 120 decreases along their respective longitudinal lengths in the direction from the proximal ends toward the distal ends, thereby causing the flexible portions 116, 126 to be more flexible than the remainder of their respective wires toward the proximal ends. In other examples, the flexible portions 116 and/or 126 can be constructed from a material that is different than the remainder of the wire toward the proximal ends. In these examples, this material is more flexible than the remainder of the length of the wires. In some examples, either or both of the flexible portions 116, 126 can be constructed of a different material in addition to having a tapered region. In other examples, the flexible portions 116 and/or 126 can be constructed from a material that is different in shape from the remainder of the length of the wires (e.g., coiled spring and the like). In some examples, the flexible portions 116, 126 can be constructed to have different thicknesses, shapes, and/or materials in order to have segments of decreased flexibility (see, e.g., 128 of FIG. 6 and FIG. 7).

By providing flexible portions 116, 126, the wires 110, 120 change shape in a predictable location (e.g., at the distal ends 114, 124). Additionally, the flexible portions 116, 126 allow a greater angled shape which is advantageous because this greater angled shape decreases the force required to form an actuated shape. In contrast, if flexible portions 116, 126 were not present, both the base wire 110 and the accessory wire 120 would be more likely to form a longer, smaller angled bow when the wires are moved relative to each other which increases the force necessary to actuate the device and may limit the size and/or shape of the vessel lumen that is accessible to the device 100 due to a different actuated shape and stress on the wires 110, 120 against a vessel wall medical device, and catheter. In addition, the flexible portions 116, 126 allow the remainder of the wires 110, 120 to have the structural integrity to contribute to directionality and maintain position in the vessel which allows placement and exchange of medical devices and catheters.

In some examples, the flexible portion 116 of the base wire 110 can have a greater rigidity (i.e., is less flexible) when actuated than the flexible portion 126 of the first accessory wire 120. As will be discussed, the difference in flexibility of the base wire 110 allows the first accessory wire 120 to arc to a greater degree when the device 100 is actuated.

The first accessory wire 120 is coupled to the base wire 110 at a distance (denoted by "L" in FIG. 1C) that is spaced away from the first distal end 114 of the base wire 110. In other words, the second distal end 124 of the first accessory wire 120 is not coupled to the base wire 110 directly at the first distal end 114; rather, this coupling is located along the longitudinal length of the base wire 110 spaced from the second distal end 124. The first accessory wire 120 can be coupled to the base wire 110 using any suitable approach, such as, welding, gluing, and the like. The first accessory wire 120 may also be an extension of a single base wire 110 that has been folded, pressed, glued or welded upon itself so that it forms a distal end 114, flexible portions 126 and 116 and two proximal ends 122 and 112.

Figures 2A, 3, 4A:
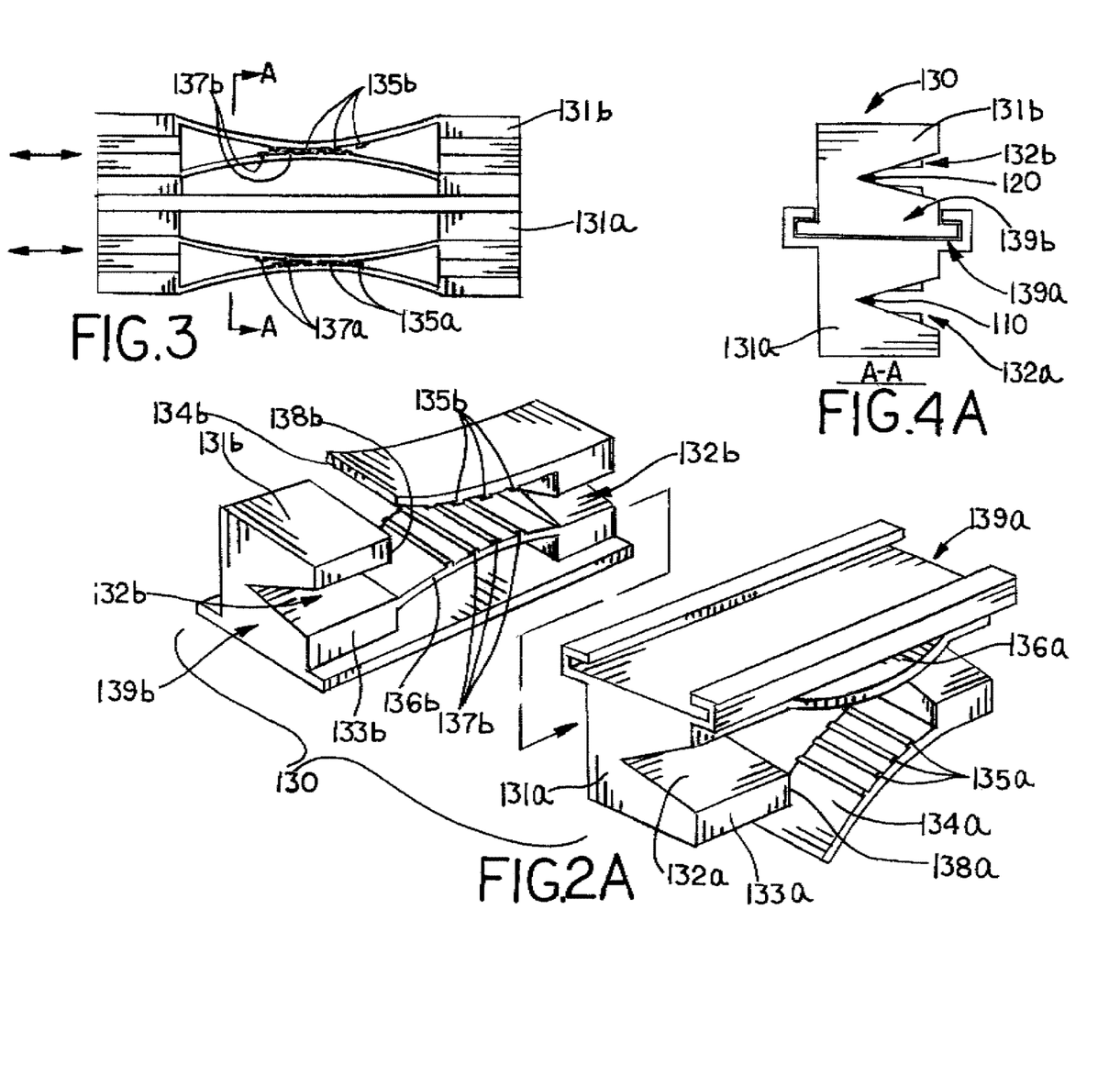
FIGS. 2A-2B are perspective exploded views of a guiding device of the medical guide wire device having a first clamping device and a second clamping device according to some aspects of the present disclosure.
FIG. 3 is a side elevation view of the guiding device of FIG. 2A, with the first clamping device operatively coupled to the second clamping device.
FIGS. 4A-B are cross-sectional views of the guiding device along the lines A-A of FIG. 2A and cross-sectional views of the guiding device along the lines A-A of FIG. 2B.
Figures 2B, 4B:
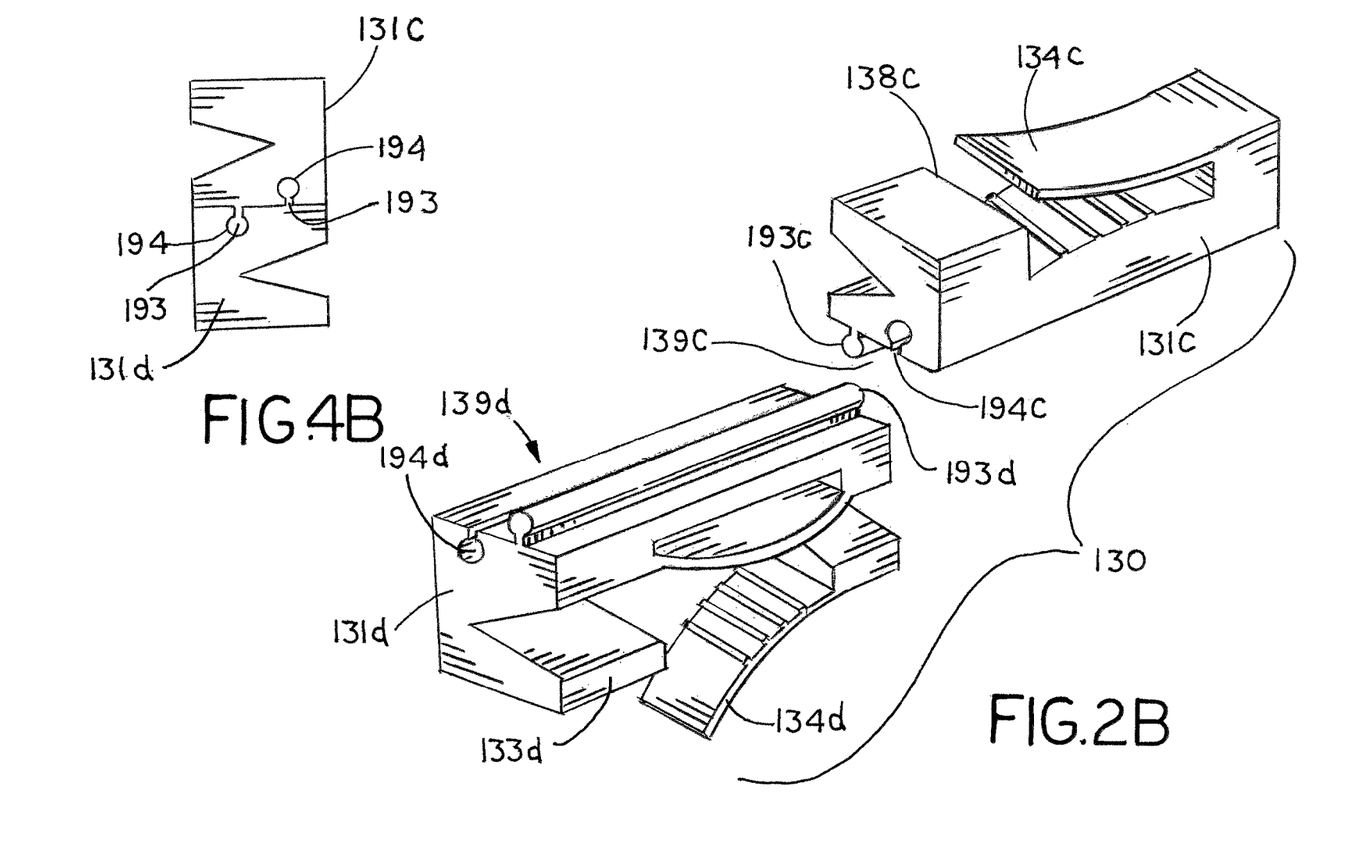

As best seen in FIGS. 2-4, the guiding device 130 is separated into two components: a first clamping device 131*a* having a body 133*a* and a second clamping device 131*b* having a body 133*b*. The first clamping device 131*a* includes a receiver slot 132*a*, a resilient tab 134*a*, a resilient clamp member 136*a*, a ledge 138*a* (that combines with the resilient tab 134*a* and the resilient clamp member 136*a* to form a first clamping portion), and a first guiding portion 139*a*. Similarly, the second clamping device 131*b* includes a receiver slot 132*b*, a resilient tab 134*b*, a resilient clamp member 136*b*, a ledge 138*b* (that combines with the resilient tab 134*b* and the resilient clamp member 136*b* to form a second clamping portion), and a second guiding portion 139*b*.

Each of the clamping devices 131*a*, 131*b* is constructed of any suitable material or materials such as, for example, polymers and/or metals. The receiver slots 132*a*, 132*b* are dimensioned to receive the wires 110, 120. Each receiver slot 132*a*, 132*b* extends along the axial length of the body 133*a*, 133*b* of the clamping device from a proximal end to a distal end of the body. Each receiver slot 132*a*, 132*b* opens outwardly along a later side of the body 133*a*, 133*b*. the base wire 116 and/or the accessory wire 126 can be slid laterally into the receiver slot 132*a*, 132*b*, respectively at the opening along the side wall and extend along the entire length of the body 133*a*, 133*b*. It is understood that either one of the first clamping device 131*a* or the second clamping device 131*b* can be coupled to either one of the base wire 110 or the first accessory wire 120 as desired. In some examples, the receiver slots 132*a*, 132*b* can include a notch or groove at a base of the slot and dimensioned to accept the wires 110, 120. Each of the resilient tabs 134*a*, 134*b* and resilient clamp members 136*a*, 136*b* can include any number of ribs 135*a*, 135*b*, 137*a*, 137*b*, respectively.

In some arrangements, the receiver slots 132*a*, 132*b* are dimensioned to receive a catheter or medical device and/or wires 110, 120.

In some arrangements, the first guiding portion 139*a* and the second guiding portion 139*b* cooperate to form an axial track and groove assembly. Specifically, in the depicted arrangement, the first guiding portion 139*a* forms a track that extends from the proximal end to the distal end along a top face of the body 133*a*. The second guiding portion 139*b* forms a groove that extends along a bottom face of the body 133*b* from the proximal end to the distal end. In some examples, the track and groove assembly may be configured in a dovetail track and groove arrangement. Other examples are possible. It is understood that either the first or second guiding portions 139*a*, 139*b* can form the track or the groove. The track and the groove slidingly interlock by coupling the first guiding portion 139*a* to the second guiding portion 139*b*, the first clamping device 131*a* slidably engages the second clamping device 131*b*, and thus the first clamping device 131*a* is slidable relative to the second clamping device 131*b* along the axes of the grooves and thus the wires.

In some arrangements best seen in FIGS. 2B and 4B, the clamping devices 131*c*, 131*d* are identical and form an axial track and groove assembly 193*cd* and 194*cd*, on the bottom face of each body from the proximal end to the distal end. The track and the groove of each guiding portion 139*c* and 139*d* slidingly interlock by coupling the first guiding portion 139*c* to the second guiding portion 139*d*, the first clamping device 131*c* slidably engages the second clamping device 131*d*, and thus the first clamping device 131*c* is slidable relative to the second clamping device 131*d* along the axes of the grooves and thus the wires.

Figure 10:
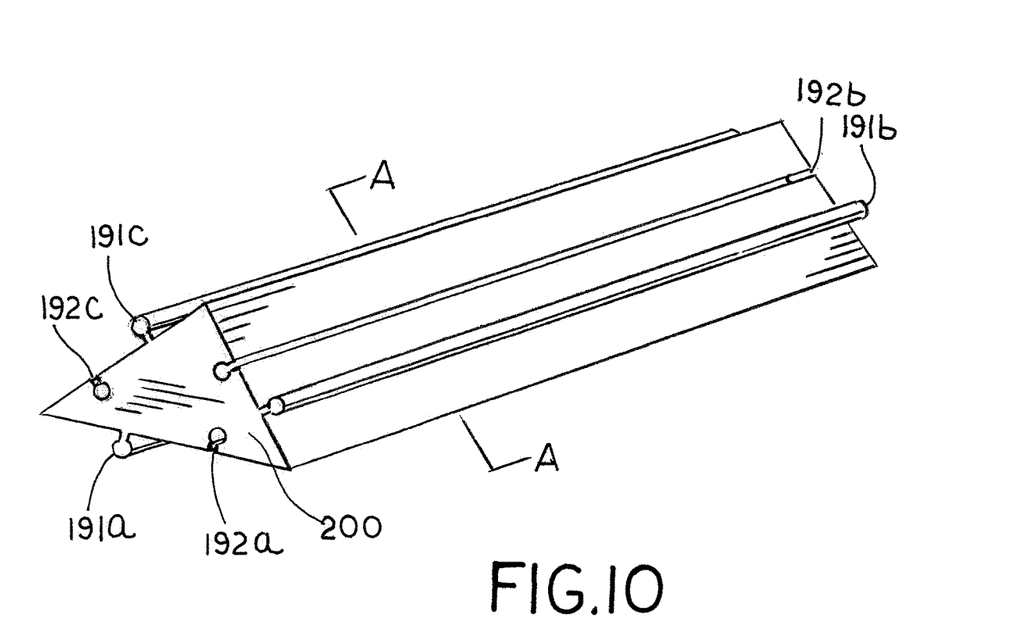
FIG. 10 is a perspective view of a common base with a number of axial tracks and grooves adapted for coupling with the guiding device of FIG. 2B.
Figures 11A, 11B:
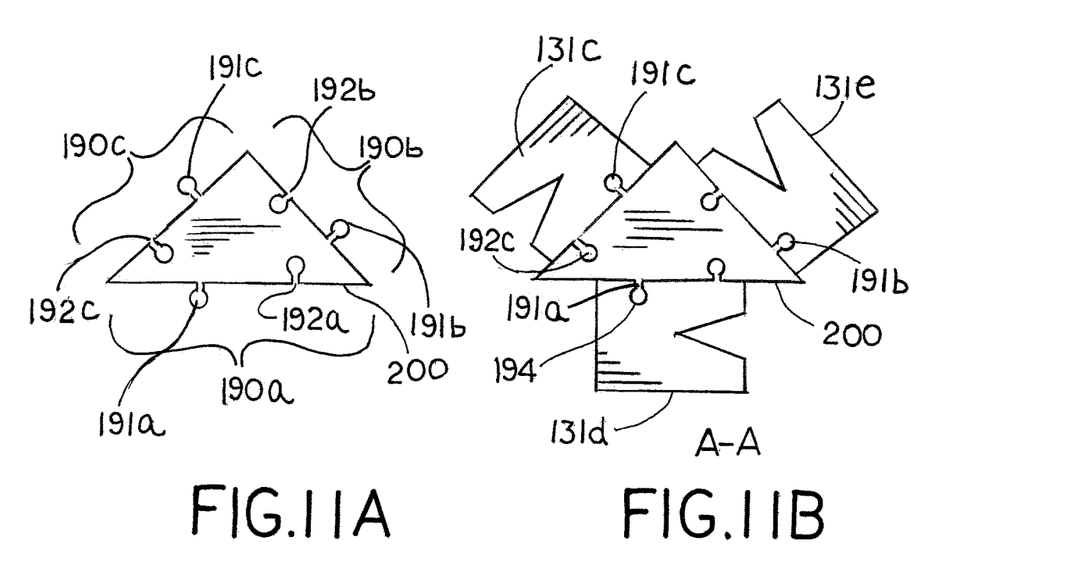
FIGS. 11A-B are cross-sectional views of a common base along the lines A-A of FIG. 10 with the guiding devices of FIG. 2B.

In some forms best seen in FIGS. 10-11B, a common base 200 containing sides with track and groove assemblies 190 A-C extending from the proximal end to the distal end. The track and the groove slidingly interlock a clamping device 131*c* with the base 200 by coupling the first guiding portion 139*c* to a track and groove assembly on a face of the base 190A, 190B or 190C, the first clamping device 131*c* slidably engages the base 200, and thus the first clamping device 131*c* is slidable relative to the base 200 along the axes of the grooves and thus the wires.

The guiding device 130 also secures to the base wire 110 and the accessory wire 120 and/or a medical device. When the resilient tabs 134*a*, 134*b* are uncoupled from the ledges 138*a*, 138*b*, the proximal ends 112, 122 of the wires 110, 120 or tubular wire, medical device, and/or catheter are inserted into the receiver slots 132a, 132b either laterally through the sidewalls or axially. The resilient tabs 134a, 134b are then urged to a closed position where they are disposed under the ledges 138a, 138b, which act to secure the resilient tabs 134a, 134b. Upon positioning the resilient tabs 134a, 134b, the resilient clamp members 136a, 136b are displaced by the wires 110, 120, tubular wire, medical device, and/or catheter. Accordingly, the resilient tabs 134a, 134b and the resilient clamp members 136a, 136b cooperate to grip or clamp the wires 110, 120, tubular wire, medical device, and/or catheter, thus maintaining the wires 110, 120, tubular wire, medical device, and/or catheter in a fixed position relative to the respective clamping device 131a or 131b. In the depicted arrangements, the ribs 135a, 135b, 137a, 137b provide additional surfaces of contact to further secure the wires 110, 120, tubular wire, medical device, and/or catheter against axial movement relative to the respective clamping device 131a or 131b. Other approaches may be used to secure the wires 110, 120, tubular wire, medical device, and/or catheter to the guiding device 130. The guiding device 130 can be removed from the wires 110, 120, tubular wire, medical device, and/or catheter by uncoupling the resilient tabs 134a, 134b from the ledges 138a, 138b, and the wires 110, 120 or catheter can then be removed.

Upon securing the base wire 110 and the first accessory wire 120 in the first and second clamping portions 1311a and 131b, respectively, as well as slidably coupling the first guiding portion 139a to the second guiding portion 139b, a user can actuate the guiding device 130 by sliding the first clamping device 131a and/or the second clamping device 131b axially along the first and second guiding portions 139a, 139b. As illustrated by FIG. 1B, as a result of slidably moving the first clamping device 131a and/or the second clamping device 131b, the flexible portion 126 of the first accessory wire 120 forms a bend or bow relative to the base wire 110. As a result, because the second distal end 124 of the first accessory wire 120 is coupled to the base wire 110, the flexible portion 116 of the base wire 110 also forms a bend. This bend causes the first distal end 114 of the base wire 110 to be redirected, that is to bend in a first direction, thereby allowing the device 100 to enter different branches of a vessel.

By coupling the second distal end 124 of the first accessory wire 120 to the base wire 110 at a distance L spaced axially from the first distal end 114, actuating the guiding device 130 imparts precise modifications to the direction of the first distal end 114 and collective shape of the distal flexible portions 116, 126.

Further, such a configuration allows for significant traversal of the wires 110, 120 through a vessel or branch vessel (otherwise known as "vessel access" or "vessel purchase") while the first accessory wire 120 is still in the bowed configuration. By offsetting the distal end 124 of the first accessory wire 120 proximally from the second end 114 along the base wire 110, the distal end 114 of the base wire 110 has a smaller profile or shape, thereby affording the distal end 114 greater access or purchase within a vessel or vessel branch. Additionally, the offset configuration allows for greater advancement of the base wire 110 into the vessel as the first accessory wire 120 is being moved back to its original, non-bowed configuration.

As discussed, the flexible portion 116 of the base wire 110 may have a greater rigidity (i.e., is less flexible) than the flexible portion 126 of the first accessory wire 120. This is advantageous as the flexible portion 126 of the first accessory wire 120 allows modifications to the direction of the first distal end 114 while the increased rigidity of 116 allows increased stabilization of vessel purchase. This important in order to maintain access when advancing a catheter or medical device over the wires 110 and 120.

Figure 5A:
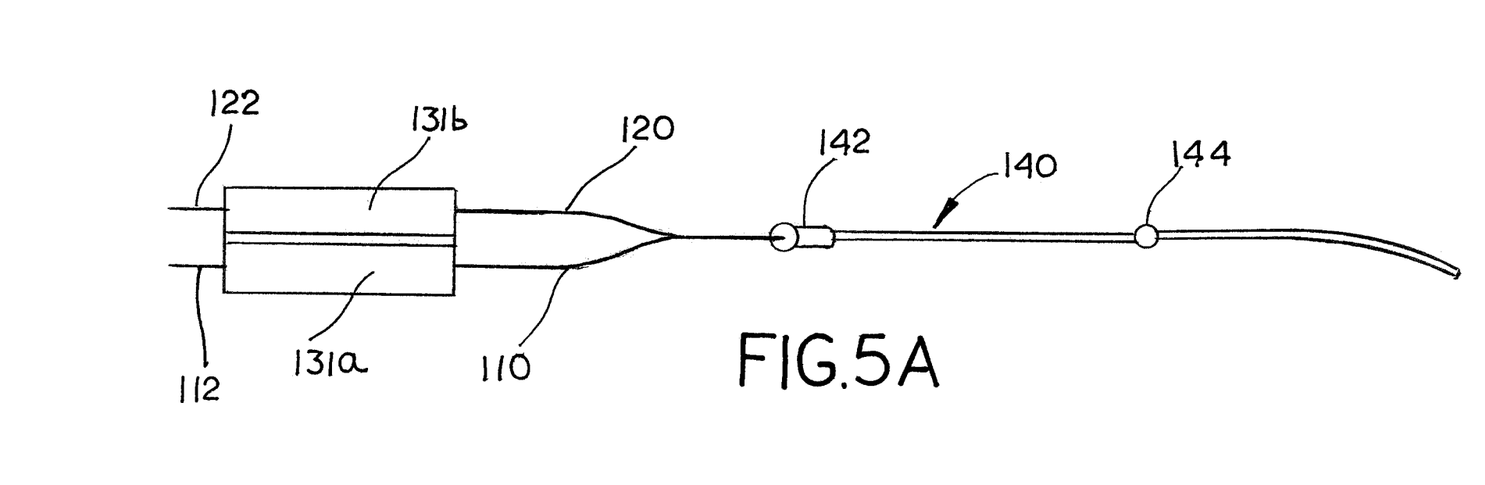
FIG. 5A is a side elevation view of the medical guide wire device in a resting position with a medical device surrounding the base wire and the accessory wire.
Figure 5B:
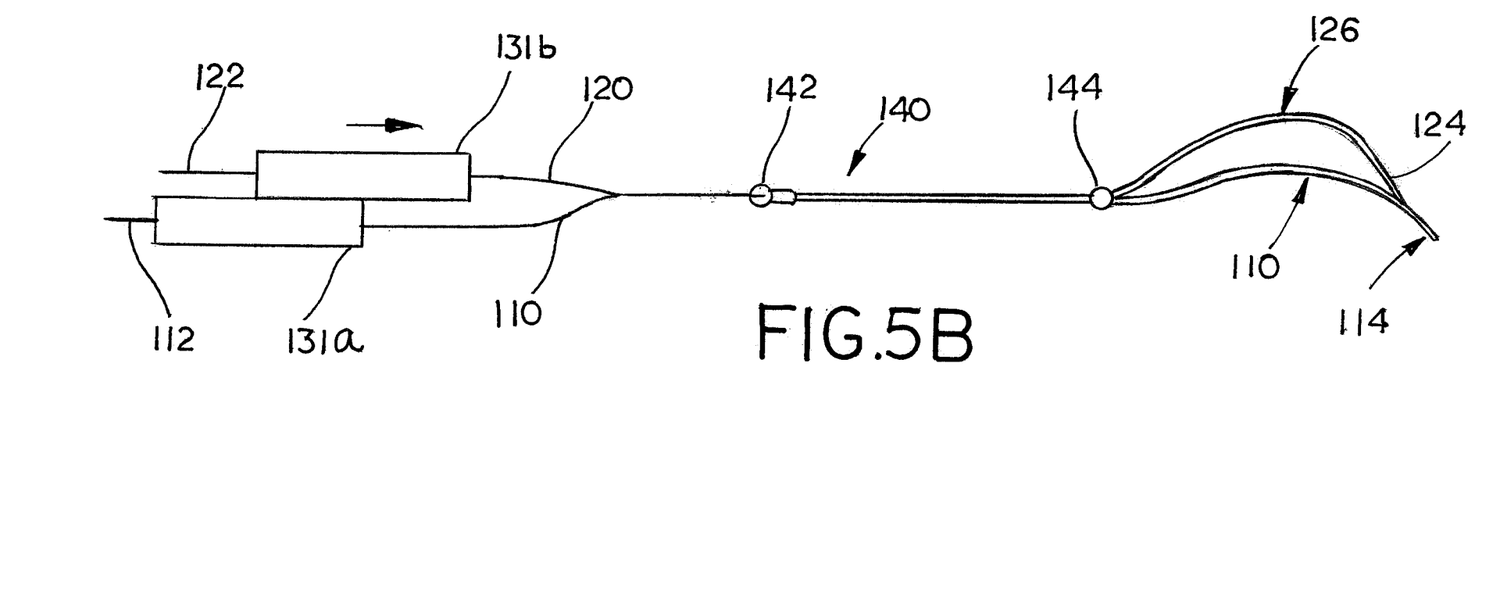
FIG. 5B is a side elevation view of the medical guide wire device of FIG. 5A in an actuated configuration.

In some approaches, and as depicted in FIGS. 5A and 5B, the medical guide wire device 100 can include a tube 140 that at least partially surrounds the base wire 110 and the first accessory wire 120. The tube 140 can be slid onto the wires 110, 120 from the proximal end by removing the guiding device 130 and inserting the proximal ends 112, 122 through an opening of the tube 140. The guiding device 130 can then be re-coupled to the wires 110, 120. This allows, for example, the tube 140 (or other medical device) to be easily slid onto the guide wires 110 and 120 while the distal end is already located inside a patient without having to withdraw the wires from the patient.

In some arrangements, the tube 140 is a medical device such as a catheter, an occlusion balloon, a sheath, or any other device designed to be placed in or near a vessel. The tube 140 can be constructed from any number of materials and can include any number of additional components 142 and/or features as desired. By using a removable guiding device 130, the tube 140 can be inserted into the vessel when the device 100 is properly positioned. In other words, in some arrangements, the device 100 can first be inserted into the vessel using the guiding device 130 while the tube 140 is not coupled to (e.g., slid over) the device 100, and upon properly positioning the wires 110, 120, the guiding device 130 can be removed from the wires 110, 120. The proximal ends 112, 122 of the wires 110, 120 can be fed through the tube 140, and the tube 140 can be inserted into the vessel by sliding the tube 140 over the wires 110, 120. Upon properly positioning the tube 140, the wires 110, 120 can be removed from the vessel.

Figure 9A:
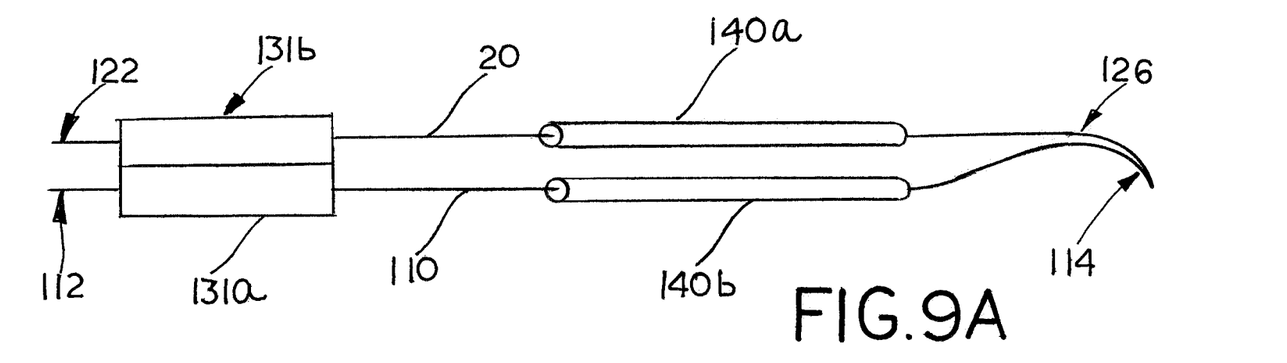
FIGS. 9A-B are side elevation views of a medical guide wire device having a tube surrounding a base wire and a tube surrounding an accessory wire for placement into a vessel.
Figure 9B:
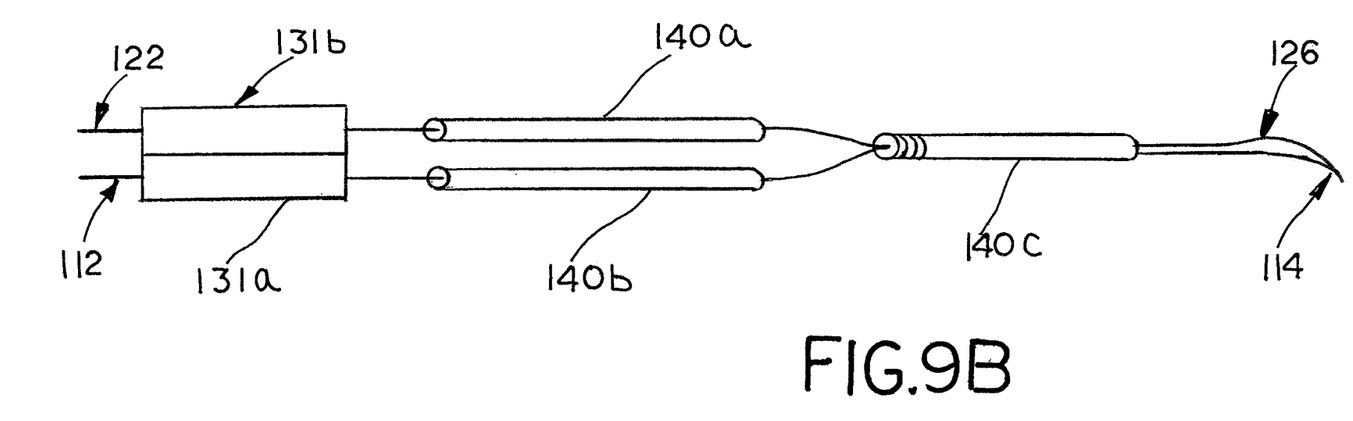

Turning to FIGS. 9A and 9B, in some arrangements, the device 100 can first be inserted into the vessel using the guiding device 130 while the tube 140 is not coupled to (e.g., slid over) the device 100, and upon properly positioning the wires 110, 120, the guiding device 130 can be removed from the wires 110, 120. The tube 140 can be formed from two distinct sections 140a, 140b. The two sections 140a, 140b may be dimensioned to occupy any desired length of either wires 110 or 120. The first section 140a may be a first medical device (e.g., a catheter) and the second section 140b may be a second medical device (e.g., an occluding balloon) which may be placed within a vessel simultaneously, saving the need for a second separate wire placement. As a result, objects such as medicines, sclerosants, and the like may be injected at different regions in the vessel. As a result, two distinct sections 140a, 140b may limit the systemic release of medications and/or protect the distal migration of a device within the vessel.

As depicted in FIG. 5B, the end 144 of the tube 140 may act as a starting point for the wires 110, 120 to bend. Thus, in some arrangements, the tube 140 can be used to provide structure and/or stability to the wires 110, 120 while traversing the vessel.

In some forms, and as illustrated in FIGS. 10-11B, the first guiding portion 131c and the second guiding portion 131d slidably engage a common base 200. The common base 200 can include a first coupling surface or guiding portion 190a, a second coupling surface or guiding portion 190b, and a third coupling surface or guiding portion 190c. It is understood that any number of coupling surfaces can be used. In some forms, the guiding portions 190a, 190b, 190c comprise an axial track 191a, 191b, 191c and groove 192a, 192b, 192c to be coupled with a groove assembly on a common removable base as part of a tubular wire, medical device, or catheter system. This is advantageous as the common base 200 can then allow the removable guiding devices to be in series on the same axial track and groove assembly on a common base (not shown) or in parallel axial tracks an grooves on the common base FIG. 11B.

Figure 6A:
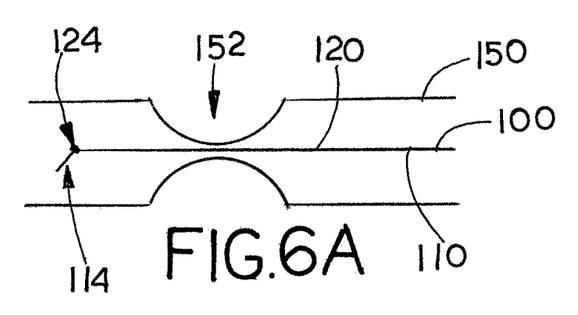
FIGS. 6A-6D are cross-sectional views of a medical guide wire device inserted into a vessel and being used to act as an anchor, stop, or plug that limits outward movement.
Figure 6B:
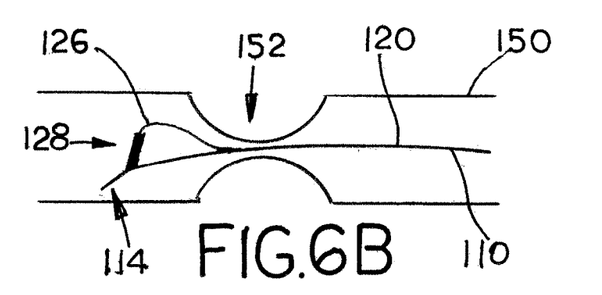
Figure 6C:
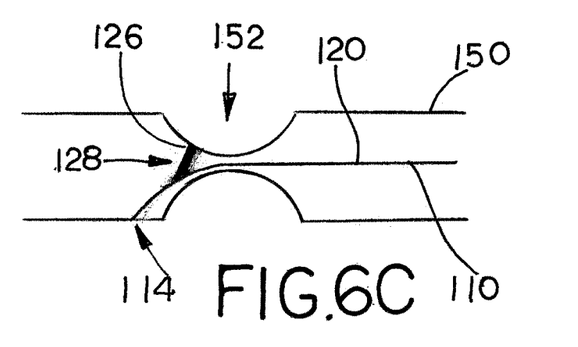
Figure 6D:
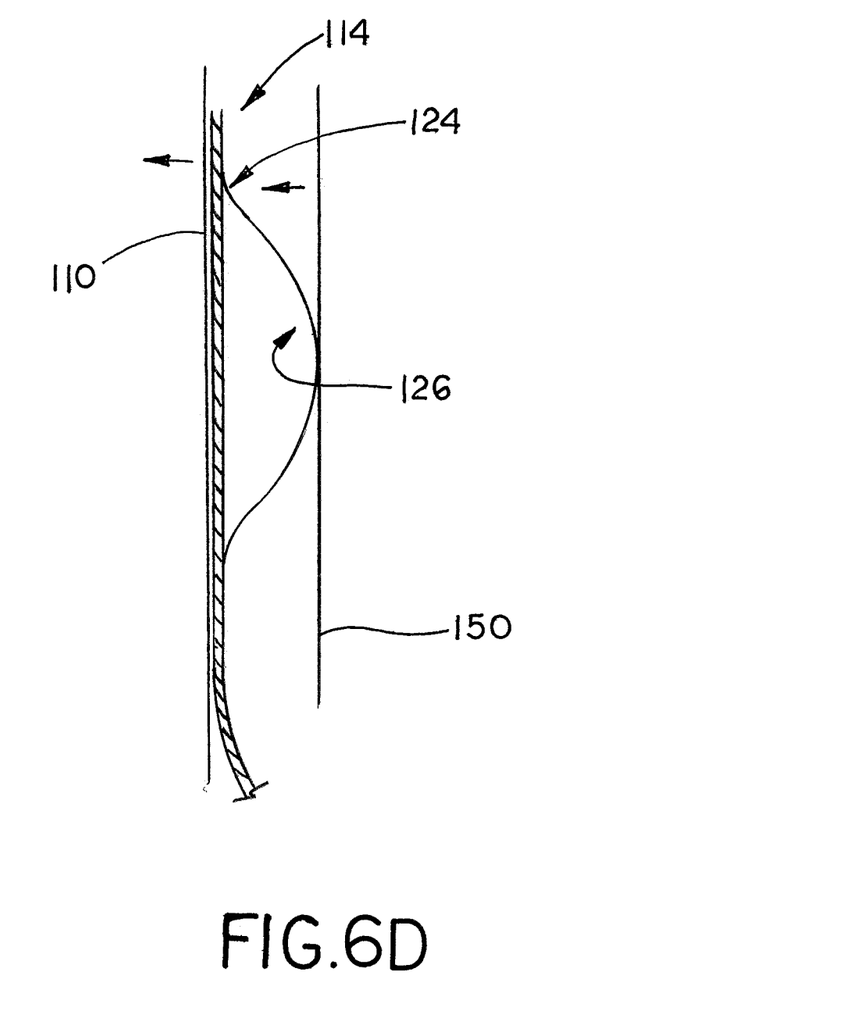

As illustrated in FIGS. 6A-6D, the device 100 can be inserted into a vessel 150 having an area 152 with a reduced diameter or stenosis due to a plaque, foreign body, tumor or clot etc. The device 100 can cause force on 152 and/or the walls of 150 as a support or brace when inserting the tube 140 (not shown). In addition, the actuated device can be forced against the area 152 and/or walls of 150 in order to strip, dissect, remove, entrap or dislodge 152. Changes to the flexible portions 126 and/or 116 allows a variety of actuated shapes such as triangles, spirals and coils. As illustrated in FIGS. 6B-6D, actuating the guiding device (not shown) causes the flexible portion 126 of the accessory wire 120 to change shape. When removing the device 100, the flexible portion 126 of the first accessory wire 120 cooperates with a part of the base wire (e.g., the flexible portion 116 and/or the first distal end 114) causing force on 152 and/or the walls of 150 potentially stripping, dissecting, removing, entrapping or dislodging 152. Most commonly this would involve removing the actuated device, and as a result all or part of 152, against an/or into a catheter or sheath.

Figures 7A, 7B, 7C:
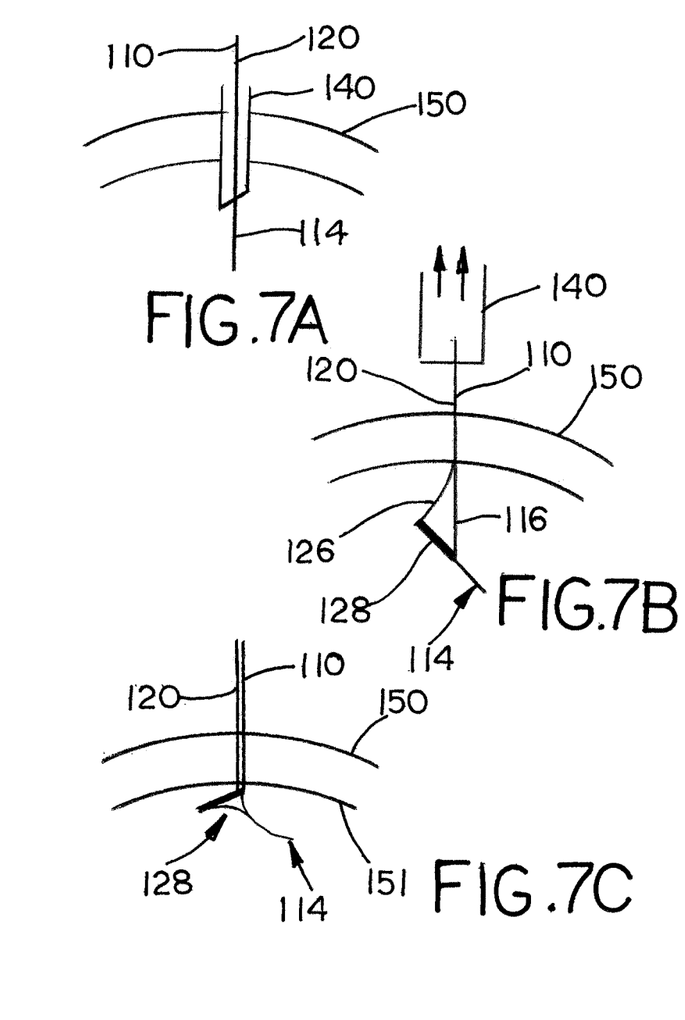
FIGS. 7A-7C are cross-sectional views of a medical guide wire device inserted through a plurality of vessel walls and device being used to act as an anchor, stop, or plug that limits outward movement.
Figures 8A, 8B, 8C, 8D, 8E, 8F:
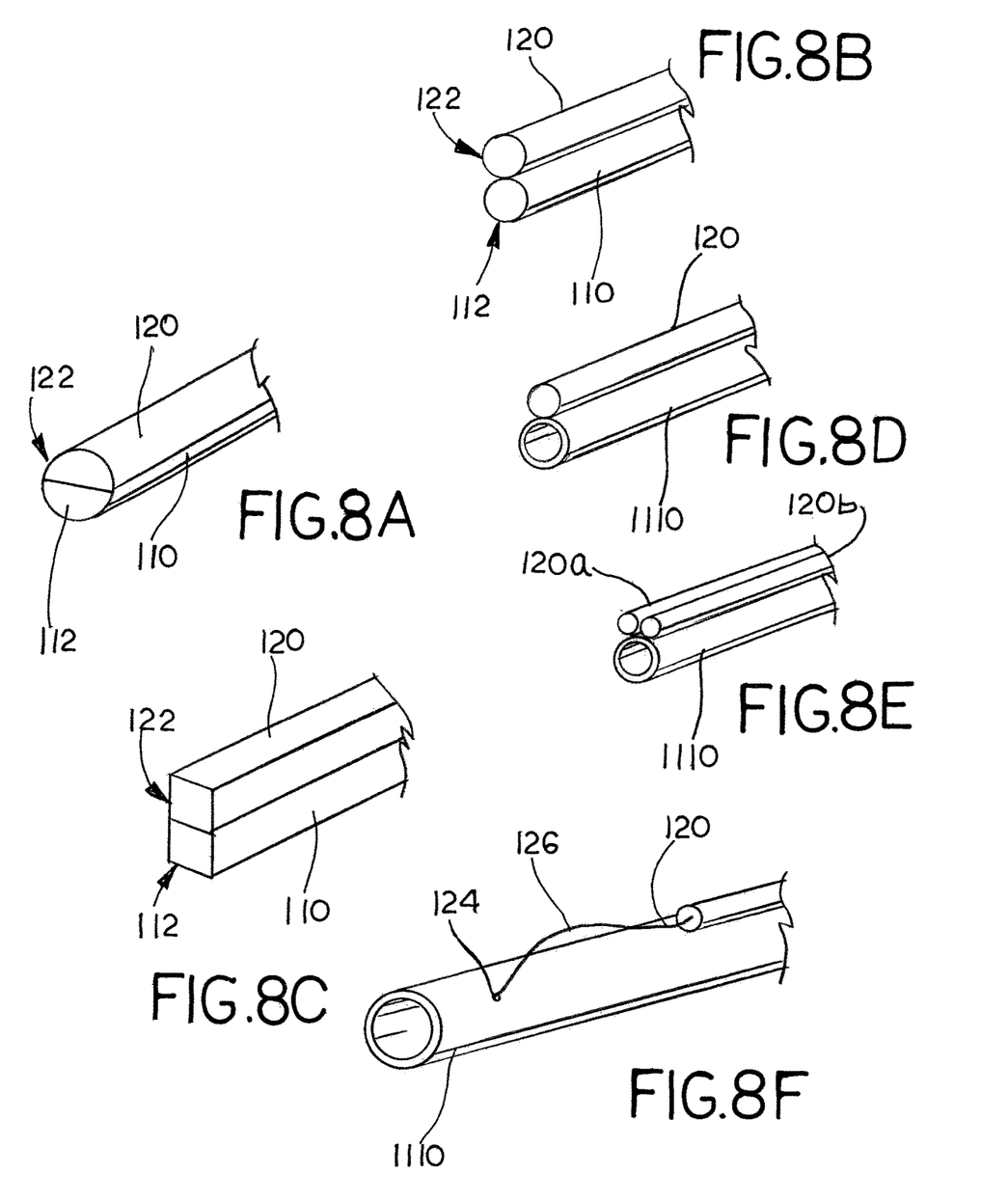
FIGS. 8A-8F are perspective views of various exemplary wires for the medical guide wire.

FIGS. 7A-7C illustrate the tube 140 (in the form of a needle) being inserted through a cavity wall or vessel 150 in a transverse direction. In FIG. 7B, the tube 140 is removed from the vessel 150, and the guiding device 130 (not shown) is actuated. In FIG. 7C, the bow formed by the flexible portion 126 contacts the cavity wall 150 and cooperates with the first distal end 114 to act as a plug to prevent removal of the guide wires 110, 120. In this example, a short region of decreased flexibility 128 within the bowing portion 126 changes the shape of the bow, which facilitates anchoring and resists removal of the device through the vessel wall 150. At this time, an additional medical device (not shown) can be inserted into the vessel lumen 151 as desired while the bow anchors the guide wires 110, 120 in place.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

A wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method of using a medical guide wire device, wherein the medical guide wire device comprises a base wire having a first proximal end, a first distal end, a longitudinal length extending therebetween, and a flexible portion near the first distal end, an accessory wire having a second proximal end, a second distal end, a longitudinal length extending therebetween, and a flexible portion near the second distal end, the second distal end of the accessory wire being coupled to the base wire near the first distal end thereof, and a guiding device comprising a first receiver configured to be removably coupled to the base wire and a second receiver configured to be removably coupled to the accessory wire, the method comprising:
   coupling the first receiver of the guiding device to the base wire at a location along its longitudinal length disposed axially between the proximal end and the distal end thereof;
   coupling the second receiver of the guiding device to the accessory wire at a location along its longitudinal length disposed axially between the proximal end and the distal end thereof;
   inserting the first distal end of the base wire and the second distal end of the accessory wire into a vessel forming an elongated cavity;
   guiding the base wire and the accessory wire through the elongated cavity with the guiding device;
   actuating the guiding device to cause the flexible portion of the base wire and the flexible portion of the accessory wire to bend; and
   advancing the base wire and the accessory wire through the elongated cavity in the direction of the bent base wire and accessory wire.

2. The method of claim 1, wherein actuating the guiding device causes the flexible portion of the accessory wire to bow and contact a sidewall of the vessel in a first direction, thereby imparting a force on the distal end of the base wire in a second direction opposite the first direction.

3. The method of claim 1, further comprising the steps of:
   removing the guiding device from the base wire and the accessory wire;
   sliding a sleeve over the first proximal end of the base wire and the second proximal end of the accessory wire.

4. The method of claim 3, wherein the sleeve comprises a medical device adapted to be at least partially inserted into the vessel, further comprising the step of recoupling the guiding device to the first proximal end of the base wire and the second proximal end of the accessory wire with the sleeve surrounding at least a portion of the base wire and the accessory wire.

5. The method of claim 1, further comprising the steps of:
   removing the guiding device from the base wire and the accessory wire;
   sliding a first sleeve over the first proximal end of the base wire; and
   sliding a second sleeve over the second proximal end of the accessory wire.

6. The method of claim 1, wherein the first distal end of the base wire and the second distal end of the accessory wire are inserted into the vessel, wherein upon actuating the guiding device, the bend in the flexible portion of the base wire and the flexible portion of the accessory wire are adapted to act as a force against the surface of a vessel and/or an intraluminal mass in order to strip, dissect, remove, entrap or dislodge an intraluminal mass.

7. The method of claim 1, wherein the first distal end of the base wire and the second distal end of the accessory wire are inserted into the vessel or cavity in a longitudinal direction, wherein upon actuating the guiding device, the bend in the flexible portion of the base wire and the flexible portion of the accessory wire are adapted to act as a plug against the vessel surface and/or stenosis of a vessel to prevent removal of the base wire and the accessory wire.

8. The method of claim 1, wherein the bend in the flexible portion of the base wire and the flexible portion of the accessory wire, when actuated, has a predetermined shape including at least one of a spiral and a coil, which then may act as a force against the surface of a vessel and/or intraluminal mass to allow stripping, dissecting, removing, entrapping or dislodging of the mass.

9. A medical guide wire device, comprising:
a base wire having a first proximal end, a first distal end, a longitudinal length extending therebetween, and a flexible portion near the first distal end;
an accessory wire having a second proximal end, a second distal end, a longitudinal length extending therebetween, and a flexible portion near the second distal end, the accessory wire being coupled to the base wire near the first distal end and the second distal end; and
a guiding device comprising a first clamping device and a second clamping device, the first clamping device having a first body, a first receiver adapted to receive the base wire extending axially through the first body, and a first clamp adapted to removably secure the base wire within the first receiver, the second clamping device having a second body, a second receiver adapted to receive the accessory wire extending axially through the second body, and a second clamp adapted to removably couple the accessory wire within the second receiver, and the first and second bodies slidably coupled so as to slide axially with respect to each other,
wherein the guiding device may be operatively coupled to the base wire and the accessory wire at a location along the longitudinal lengths disposed axially between the proximal ends and the distal ends thereof, and;
wherein upon actuating the guiding device by sliding at least one of the first and second clamping devices axially with respect to the other of the first and second clamping devices when operatively coupled to the respective base wire and accessory wire, the flexible portion of the base wire and the flexible portion of the accessory wire form a curve at the first distal end of the base wire and the second distal end of the accessory wire.

10. The medical guide wire device of claim 9, wherein:
the first clamping device includes a first guiding portion, and
the second clamping device includes a second guiding portion,
wherein the second guiding portion is adapted to slidably couple and interlock with the first guiding portion of the first clamping device.

11. The medical guide wire device of claim 10, wherein the first guiding portion and the second guiding portion comprises an axial track and groove assembly.

12. The medical guide wire device of claim 11, wherein the axial track and groove assembly comprises a dovetail track adapted to be coupled with a dovetail groove.

13. The medical guide wire device of claim 9, wherein the flexible portion of the base wire and the flexible portion of the first accessory wire comprise a tapered region of reducing wire thickness.

14. The medical guide wire device of claim 9, wherein the flexible portion of the base wire and the flexible portion of the accessory wire comprise a region constructed of a different material than the remainder of the base wire and the accessory wire.

15. The medical guide wire device of claim 9, wherein the flexible portion of the base wire and the flexible portion of the accessory wire comprise a region constructed of a different shape than the remainder of the base wire and the accessory wire.

16. The medical guide wire device of claim 9, further comprising a tube at least partially surrounding the base wire and the accessory wire, wherein the tube may be mounted to the base wire and the accessory wire by removing the guiding device and inserting the proximal end of the base wire and the proximal end of the accessory wire through the tube.

17. The medical guide wire device of claim 9, wherein a plurality of tubes at least partially surround at least one of the base wire and the accessory wire.

18. The medical guide wire device of claim 9, wherein the second distal end of the accessory wire is coupled to the base wire at a distance spaced apart from the first distal end;
wherein upon actuating the guiding device the flexible portion of the accessory wire forms a bow and causes the flexible portion of the base wire to form a curve.

19. The medical guide wire device of claim 18, wherein the flexible portion of the base wire has a greater rigidity than a rigidity of the flexible portion of the accessory wire.

20. The medical guide wire device of claim 18, wherein the flexible portion of the base wire and the flexible portion of the accessory wire comprise at least one of a tapered portion of reduced wire thickness, a secondary material that is different from a primary wire material, and a shape that results in a change in flexibility.

21. The medical guide wire device of claim 18, wherein each of the base wire and the accessory wire each form a cross-sectional shape selected from one of the following: circular, semi-circular, triangular, tubular, and rectangular.

22. The medical guide wire device of claim 18, wherein at least one of the base wire and the accessory wire is coated with at least one of a hydrophilic material and a nonconductive material.

23. The medical guide wire device of claim 18, wherein the accessory wire is adapted to exert a force on the flexible portion of the base wire thereby causing the base wire to form the curve.

24. A guiding device configured to be releasably coupled to a medical guide wire assembly comprising a first wire and a second wire, the guiding device comprising:
a first clamping device comprising a first body, a first receiver defined by the first body and adapted to receive the first wire extending axially through the first body from a proximal end of the first body to a distal end of the first body, and a first clamp adapted to removably secure the first wire within the first receiver;
a second clamping device comprising a second body, a second receiver defined by the second body and adapted to receive the second wire extending axially through the second body from a proximal end of the second body to a distal end of the second body, and a second clamp adapted to removably couple the accessory wire within the second receiver;
wherein the first and second bodies are slidably coupled with each other so as to slide axially with respect to each other; and
wherein the guiding device may be operatively coupled to the first wire and the second wire at a location along the longitudinal lengths disposed axially between the proximal ends and the distal ends thereof, and;

wherein the guiding device is configured to control a curvature of the medical guide wire assembly when operatively coupled to the respective first wire and second wire by sliding at least one of the first and second clamping devices axially with respect to the other of the first and second clamping devices.

* * * * *